United States Patent [19]

Stern et al.

[11] Patent Number: 4,554,397

[45] Date of Patent: Nov. 19, 1985

[54] PROCESS FOR MANUFACTURING A LINEAR OLEFIN FROM A SATURATED FATTY ACID OR FATTY ACID ESTER

[75] Inventors: Robert Stern, Paris; Gérard Hillion, Herblay, both of France

[73] Assignee: Institut Francais du Petrole, Rueil-Malmaison, France

[21] Appl. No.: 643,936

[22] Filed: Aug. 24, 1984

[30] Foreign Application Priority Data

Aug. 25, 1983 [FR] France ................................ 83 13822

[51] Int. Cl.[4] ............................................. C07C 1/00
[52] U.S. Cl. .................................... 585/638; 585/639; 585/640
[58] Field of Search ......................... 585/638, 639, 640

[56] References Cited

U.S. PATENT DOCUMENTS

| | | | |
|---|---|---|---|
| 3,079,413 | 2/1963 | Moulton et al. | 585/638 |
| 3,530,198 | 9/1970 | Fenton | 585/638 |
| 3,956,408 | 5/1976 | Schell et al. | 585/639 |
| 4,373,109 | 2/1983 | Olah | 585/639 |

*Primary Examiner*—D. E. Gantz
*Assistant Examiner*—Chung K. Pak
*Attorney, Agent, or Firm*—Millen & White

[57] ABSTRACT

A linear olefin is manufactured by contacting a fatty acid or ester with a catalyst comprising nickel and at least one metal from the group consisting of tin, germanium and lead at 200°–400° C.

14 Claims, No Drawings

PROCESS FOR MANUFACTURING A LINEAR OLEFIN FROM A SATURATED FATTY ACID OR FATTY ACID ESTER

It is known to manufacture olefins from saturated fatty acids by using, as catalysts, noble metals in the presence of phosphines. Thus FOGLIA and BARR, JAOCS 53, 737 (1976), decarbonylate stearic acid at 280° C. in the presence of rhodium phosphine complexes and an excess of a phosphine of the triphenylphosphine type. They obtain heptadecene.

Similarly, FENTON in U.S. Pat. No. 3,530,198 obtains olefins from fatty acids by operating with palladium chloride in the presence of lithium chloride and various phosphines.

These catalytic processes do not seem, a priori, of economic value for two reasons: the first is the investment cost in catalyst, the second is the lack of stability of the catalysts.

In U.S. Pat. No. 4,102,938, vegetable oil is pyrolized in the presence of mixed oxides of various metals. The resultant complex mixture contains olefins and saturated hydrocarbons, ketones, sometimes aromatic hydrocarbons and mainly cracking products. It is practically impossible to extract an olefin from this mixture.

When considering more particularly nickel catalysts, it is observed that, at temperatures higher than 200° C., they tend to generate cracking products or, as mentioned in W. F. MAIER, Chem. Ber. 115, 808–812 (1982), saturated hydrocarbons by decarboxylation under atmospheric pressure at 180° C. Thus, by passing octoic acid in the gas phase over a nickel catalyst in the presence of hydrogen, a 64% heptane yield is obtained, which does not represent a high added value.

Various authors have heated stearic acid with Raney nickel and obtained a gas mixture containing CO and mainly $CO_2$, an ethylenic acid, stearone, nickel stearate and 15% of unidentified ethylenic hydrocarbons. The major part of nickel was present as nickel stearate after 200 hours at 200°–230° C.

Thus nickel appears as able either to catalyze the manufacture of saturated hydrocarbons or to induce the formation of complex mixtures, while being consumed.

Thus, apparently, no process exists, using a non noble metal, whereby linear olefins can be selectively obtained from linear carboxylic acids or esters.

It has now surprisingly been found that, by using a nickel-tin, nickel-germanium and/or nickel-lead catalyst, and operating preferably in the presence of hydrogen, carboxylic acid and esters are converted to olefins with a remarkable selectivity. The olefins have one carbon atom less than the acid or the acid portion of the ester. By distillation, there is recovered from the top fractions an alcohol corresponding to the alcohol portion of the ester, when the alcohol is sufficiently stable, or water when the starting material is an acid.

The content of undesirable cracking products is very low, sometimes nil. It is thus possible to obtain an olefin yield averaging, under optimal conditions, the theoretical yield.

This constitutes a new way of economically manufacturing unbranched linear olefins whose double bond is mainly in 1 position, with a variable proportion of olefins with the double bond in another position, essentially 2, 3 and/or 4. This way may be used in competition with the manufacture of linear olefins from ethylene by oligomerization, since the price of ethylene is only slightly lower than that of certain saturated vegetable or animal oils or fats.

This reaction is applicable particularly to saturated linear carboxylic acids having from 6 to 30 carbon atoms, as well as to esters formed between these acids and mono- or polyhydric alcohol, for example monoalcohols having 1 to 4 carbon atoms, glycols and glycerol, and to glycerol partial esters. Said starting materials are, for example, saturated oils consisting of esters of glycerine and saturated fatty acids, or preferably lower alcohol esters, for example the methyl, ethyl, propyl or butyl esters of fatty acids derived from tallow, palm oil, the palm solid fraction, coprah, babassu or palm-cabbage oil, or obtained by complete hydrogenation of oil or fat or esters of unsaturated oils. The esters of lower alcohols may be obtained, for example, by transesterification of oils or fats or by esterification of the corresponding fatty acids. Examples of saturated fatty acids are those obtained by fractional crystallization of the fatty acids from tallow.

SUMMARY OF THE INVENTION

The object of the invention is specifically to obtain olefins by using a catalyst consisting of nickel and a metal selected from the tin, germanium and/or lead group and more particularly by using a nickel-tin catalyst.

The above-mentioned catalytic system has original properties since other tested metal pairs are inert or result mainly in the production of cracking or decarboxylation products. The presence of hydrogen is necessary to maintain the activity of the catalyst. But it is possible to use an inert gas for a certain time. The reaction conditions are relatively broad since the temperature ranges from 200° to 400° C., preferably from 300° to 380° C. The pressure may be the atmospheric pressure or a higher pressure. Particularly when the acids or esters are too volatile, it is convenient to operate under super-atmospheric pressure in order to maintain a liquid phase. However, the reaction may take place as well in gas phase as in liquid phase and may be performed either batchwise or continuously.

The VVH is preferably from 0.1 to 10 vol/vol/hour when considering the liquid phase.

Finally, additives can be added to the above-mentioned catalyst, for example sulfur derivatives to decrease the hydrogenating power of nickel and make the reaction more selective. Other additives, based on arsenic or phosphorus, can be used.

The catalyst may be prepared by addition of a tin, germanium of lead compound to Raney nickel or to supported nickel. The nickel carriers are preferably non acidic, as for example silicas of low and high surface area, titanium oxide, zinc oxide and certain aluminas of low surface area or alkalized. When nickel is supported, its proportion is, for example, from 1 to 50% by weight of the whole catalyst (Ni+carrier).

Examples of tin compounds are bivalent or tetravalent tin halides, alkali or alkaline-earth metal stannates, nickel stannate, or preferably hydrocarbyl tin compounds. Examples of hydrocarbyl tin compounds are tetramethyl tin, tetrabutyl tin, tetrapropyl tin, tetraphenyl tin and dibutyl tin dilaurate. Examples of lead compounds are tetraethyl lead, tetramethyl lead, trimethyl lead acetate, triethyl lead acetate, tetraphenyl lead and tetrabutyl lead or lead chlorides, silicates or carboxylates. Examples of germanium compounds are germanium chlorides, tetramethyl germanium, tetraphenyl germanium and tetrabutyl germanium.

The ratio by weight $(Sn+Ge+Pb)/Ni$ is usefully from 0.001:1 to 10:1 and preferably from 0.05:1 to 1:1.

The catalyst is preferably manufactured by impregnating solid nickel (Raney nickel of supported nickel) with a tin, germanium or lead compound, preferably in a boiling solvent, or by impregnating a carrier with a common solution of the metals or with separate solutions of the nickel compound and the additional metal compound. Another method consists of passing a hydrocarbyl tin, lead or germanium compound in a column containing nickel in reduced form. When the additional metal compound is liquid, a solvent is not necessary. Water can be used as solvent when it does not decompose the metal compound. With hydrocarbyl compounds an anhydrous medium is used, for example a hydrocarbon medium. When the additional metal is used as hydrocarbyl metal compound, it is unnecessary to proceed to other operations after impregnation, except washing out the unreacted compound with hydrocarbon. When the additional metal is in ionized form, reduction at high temperature is preferably performed, for example at 400°–500° C. in a hydrogen stream. In some cases, nickel and the additional compound can be reduced simultaneously. The reduction may be performed with hydrogen or with reducing agents of the alkyl aluminum type, with sodium hydrides or with other known chemical reducing agents.

In a final step, the catalyst may be impregnated with a hydrogenation inhibitor. The later may be a sulfur compound, for example a mercaptan, a disulfide, thiophene or hydrogen sulfide. The sulfur compound may be introduced in admixture with the charge during the reaction. As the sulfur compounds are frequently volatile at the temperature at which the reaction is conducted, the catalyst may be previously impregnated and traces of sulfur compounds may be continuously added.

The amount of sulfur thus introduced are advantageously from 0.001 to 5% of the nickel weight, preferably from 1 to 3% of the nickel weight.

Phosphorus compounds, such as phosphines, or arsenic compounds may be used, instead of sulfur compounds. Examples of such phosphorus compounds are aromatic phosphines.

When the conversion of the ester or acid is not complete, the olefins may be easily separated by distillation while recycling the distillation residue containing the unreacted acid or ester.

The resultant olefin is a good substrate for hydroformylation or for manufacturing alkyl aromatics.

EXAMPLES

The following examples illustrates the invention. VPC is the abbreviation for vapor phase chromatography.

EXAMPLE 1

A drum provided with a distillation system is successively fed with 50 g of palmitic acid, 10 g of dry Raney nickel in cyclohexane and 870 mg of tetrabutyl tin. The mixture is slowly heated while distilling the cyclohexane and passing a hydrogen stream, the drum being brought to a temperature of 300°–310° C. A liquid product distills at 210°–230° C. At time intervals, additional amounts of palmitic acid, totalling 150 g, are injected into the drum, while distilling progressively a product which, as shown by VPC analysis, consists mainly of a mixture of differently positioned isomers of linear pentadecene, comprising about 60% of 1-pentadecene. Some pentadecane has formed. The $C_{15}$ olefin weight is 63.5 g; the selectivity to $C_{15}$ olefin is 69% with respect to the converted acid.

EXAMPLE 2 (comparative)

10 g of Raney nickel are heated with 50 g of palmitic acid and the operation is conducted as in Example 1, except that tin is omitted. After introduction of 83 g of palmitic acid as a total, 46.7 g of distilled liquid are recovered which contain only 3.5 g of pentadecene, the major part consisting of cracking products. The selectivity with respect to the converted acid is 6%.

It is thus apparent that the introduction of tin has multiplied by ten the olefin yield.

EXAMPLE 3

50 g palmitic acid and 10 g of a catalyst containing 25% of nickel on silica are heated with 217 mg of tetrabutyl tin. Instead of passing hydrogen, argon is passed at a rate of 100 cc/min. Between 280° and 320° C., 32 g of a liquid of low acidity (9.3% of palmatic acid) distills. This product consists mainly of linear pentadecene and pentadecane. The selectivity to pentadecene is 71%.

EXAMPLE 4

In order to show the specificity of nickel, and particularly of the nickel-tin pair, various catalysts have been tested.

The results obtained with 100 g of palmitic acid, while operating as in Example 1, are reported in the following table:

| Catalyst | Distilled product in g | Selectivity to $C_{15}$ olefin | Remark |
|---|---|---|---|
| Raney cobalt (10 g) + tetrabutyl tin (0.87 g) | foam | 2% | cobalt palmitate, cracking |
| Raney iron (10 g) + tetrabutyl tin (0.87 g) | profuse foam | $\leq 0.5\%$ | ketone, complete decarboxylation |
| Copper chromite (10 g) | 35 | 1–2% | low activity, cracking |
| Palladium on carbon at 5% 10 g | 30 | traces | low activity, cracking to satured hydrocarbon |
| Nickel-tin 10 g (Catalyst of example 1) | 71 | 65% | no cracking |

EXAMPLE 5

The catalyst of Example 1 is used with hydrogenated palm ethyl ester as subtrate. Mainly linear pentadecene and heptadecene, isomerized to a small extent, are formed. The molar yield to olefin is 49% with respect to the total ester and the selectivity is 71%.

EXAMPLE 6 (comparison)

Example 2 is repeated, but with hydrogenated palm ethyl ester. The yield is only 3% of a mixture of linear pentadecene and heptadecene and the selectivity is lower than 5%.

EXAMPLE 7

Example 1 is repeated but with a mixture of palmitic and stearic acids ethyl esters and with the further addition to the catalyst of 1% dibutyl sulfur with respect to nickel. $C_{15}$ and $C_{17}$ linear olefins are obtained with a yield to olefin of 47%; the ratio olefin/saturated hydrocarbon is higher than 100 and the selectivity with respect to the converted ester is 85%.

EXAMPLE 8

A methyl ester of stearic acid is introduced continuously at 370° C. in a tube containing a catalyst of nickel on silica previously impregnated with tetrabutyl tin as in Example 3 and with dibutyl sulfur as in Example 7.

A molar conversion of 72% of the ester to linear olefin is obtained at a VVH of 0.66. The olefin does not contain any cracking product.

The balance is as follows:

| | |
|---|---|
| Ester conversion: | 83% |
| Heptadecene with respect to the converted ester: | 85.5% |
| Heptadecane with respect to the converted ester: | 11% |
| $C_{31}$, $C_{33}$ and $C_{35}$ ketones with respect to the converted ester: | 3% |

EXAMPLE 9

Example 8 is repeated but with ethyl laurate. The ratio olefin/saturated compound is 17. However the conversion is low: 21% of the ester was converted to a very pure linear olefin easy to distill and to separate from the unconverted ester.

What is claimed as the invention is:

1. A process for manufacturing olefins, comprising contacting a carboxylic acid or a carboxylic ester with a catalyst at a temperature from 200° to 400° C., wherein the catalyst simultaneously contains nickel and at least one metal from the group consisting of tin, germanium and lead.

2. A process according to claim 1, wherein the catalyst results from the impregnation of Raney nickel or of supported nickel with a solution of at least one compound of said at least one metal.

3. A process according to claim 2, wherein said at least one compound is a hydrocarbyl tin compound, a hydrocarbyl germanium compound or a hydrocarbyl lead compound.

4. A process according to claim 3, wherein the tin compound is an alkyl tin compound.

5. A process according to claim 1, wherein the catalyst results from the impregnation of a carrier by a common solution of at least one nickel compound and at least one compound of said at least one metal, or from the impregnation of a carrier, successively with a solution of a nickel compound and a solution of said at least one compound.

6. A process according to claim 1, wherein the catalyst further contains a sulfur, phosphorus or arsenic compound.

7. A process according to claim 1, wherein the carboxylic acid or the carboxylic ester is linear.

8. A process according to claim 1, conducted at 300°-380° C.

9. A process according to claim 4, conducted at 300°-380° C.

10. A process according to claim 1, wherein the weight ratio of said at least one metal to nickel is 0.001:1 to 10:1.

11. A process according to claim 1, wherein the weight ratio of said at least one metal to nickel is 0.05:1 to 1:1.

12. A process according to claim 4, wherein the weight ratio of said tin to nickel is 0.05:1 to 1:1.

13. A process according to claim 8, wherein the weight ratio of said at least one metal to nickel is 0.05:1 to 1:1.

14. A process according to claim 9, wherein the weight ratio of said tin to nickel is 0.05:1 to 1:1.

* * * * *